United States Patent
Elder et al.

(10) Patent No.: US 9,383,332 B2
(45) Date of Patent: Jul. 5, 2016

(54) ANALYTICAL TEST STRIP WITH INTEGRATED BATTERY

(71) Applicant: LifeScan Scotland Limited, Inverness-shire (GB)

(72) Inventors: David Elder, Inverness (GB); Stanley Young, Inverness (GB); Brian Guthrie, Inverness (GB); John Young, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 416 days.

(21) Appl. No.: 14/034,990

(22) Filed: Sep. 24, 2013

(65) Prior Publication Data

US 2015/0083609 A1 Mar. 26, 2015

(51) Int. Cl.
G01N 27/327 (2006.01)

(52) U.S. Cl.
CPC .................... G01N 27/3272 (2013.01)

(58) Field of Classification Search
CPC .............. C12Q 1/00; C12Q 1/02; C12Q 1/34; C12Q 1/54; G01N 27/327; G01N 27/3272; G01N 27/48; G01N 27/26; G01N 33/487; A61B 5/05; A61B 5/14532
See application file for complete search history.

(56) References Cited

U.S. PATENT DOCUMENTS

| | | | |
|---|---|---|---|
| 6,217,744 B1 | 4/2001 | Crosby | |
| 6,743,635 B2 | 6/2004 | Neel et al. | |
| 7,291,256 B2 | 11/2007 | Teodorczyk et al. | |
| 7,867,369 B2 | 1/2011 | Bhullar et al. | |
| 7,955,856 B2 | 6/2011 | Neel et al. | |
| 8,388,905 B2 | 3/2013 | Neel et al. | |
| 8,394,246 B2 | 3/2013 | Celentano et al. | |
| 2003/0111357 A1 | 6/2003 | Black | |
| 2005/0023137 A1* | 2/2005 | Bhullar ................. | C12Q 1/001 204/403.1 |
| 2005/0158704 A1 | 7/2005 | Tyvoll et al. | |
| 2007/0193882 A1 | 8/2007 | Dai et al. | |
| 2008/0021519 A1 | 1/2008 | De Geest et al. | |
| 2009/0301899 A1 | 12/2009 | Hodges et al. | |
| 2010/0094367 A1 | 4/2010 | Sen | |
| 2010/0213080 A1* | 8/2010 | Celentano ............ | A61B 5/0002 205/777.5 |
| 2011/0057671 A1 | 3/2011 | Welsh et al. | |

FOREIGN PATENT DOCUMENTS

WO 2006009404 A1 1/2006
WO WO 2012125494 A2 9/2012

OTHER PUBLICATIONS

International Search Report and Written Opinion issued in related International Patent Application No. PCT/EP2014/070249, mailed Nov. 28, 2014, 8 pages.

* cited by examiner

*Primary Examiner* — Jennifer Dieterle

(57) ABSTRACT

A test strip for use with an analyte meter comprises an integrated power source, such as a battery wherein the test strip is configured upon insertion into the meter to provide sufficient power for completing a sample assay without requiring a separate power source in the meter.

20 Claims, 5 Drawing Sheets

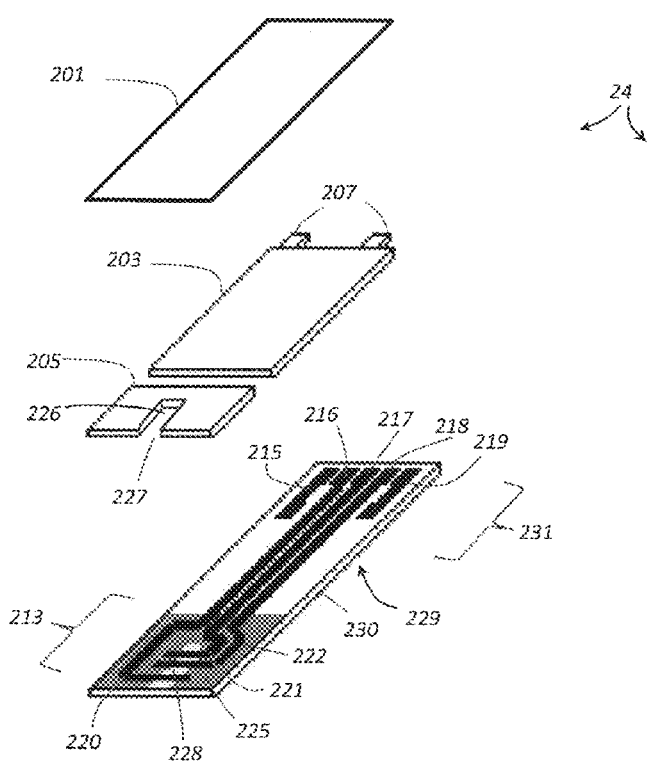
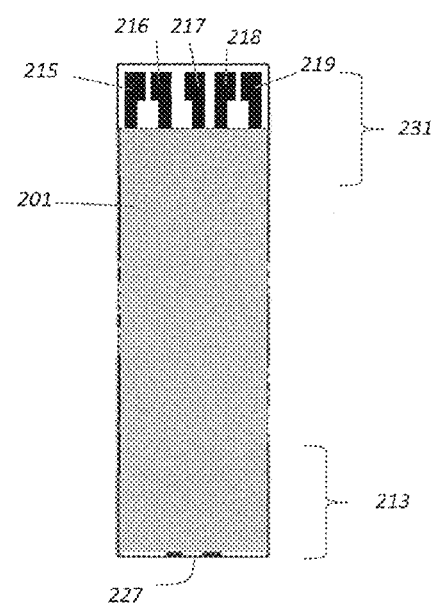
FIG. 2A
FIG. 2B

ANALYTICAL TEST STRIP WITH INTEGRATED BATTERY

TECHNICAL FIELD

The application relates generally to the field of analytical test strips used in portable test meters, such as those used for measuring blood glucose, and, in particular, to analytical test strips capable of providing electrical power for performing these measurements.

BACKGROUND

Analyte detection in physiological fluids, e.g., blood or blood-derived products, is of ever increasing importance for people who require monitoring of their analyte levels. Blood analyte measurement systems typically comprise an analyte meter that is configured to receive a biosensor, usually in the form of a test strip. A user may obtain a small sample of blood typically by a fingertip skin prick and then may apply the sample to the test strip to begin a blood analyte assay. Because many of these systems are portable, and testing can be completed in a short amount of time, patients are able to use such devices in the normal course of their daily lives without significant interruption to their personal routines. A person with diabetes may measure their blood glucose levels several times a day as a part of a self management process to ensure glycemic control of their blood glucose within a target range. Analyte detection assays find use in a variety of applications, including clinical laboratory testing, home testing, etc., where the results of such testing play a prominent role in diagnosis and management in a variety of disease conditions. Analytes of interest include glucose in diabetes management, cholesterol, and the like. In response to this growing importance of analyte detection, a variety of analyte detection protocols and devices have been developed for both clinical and home use.

One type of system that allows people to conveniently monitor their blood glucose levels includes a biosensor (e.g., a disposable test strip) for receiving a blood sample from a user, and a meter that reads the test strip to determine the glucose level in the blood sample. The test strip typically includes electrical contact pads, for engaging electrical contacts of the meter, and a sample chamber that contains reagents (e.g., glucose oxidase and a mediator) and electrodes to form an electrochemical cell. To begin the test, the test strip is inserted into the meter and the user applies a blood sample to the sample chamber. The analyte is allowed to react with the redox reagent to form an oxidizable (or reducible) substance in an amount corresponding to the blood analyte concentration. The quantity of the oxidizable (or reducible) substance present is then estimated electrochemically by applying a voltage signal to the reacted sample via the electrodes and measuring an electrical response which is related to the amount of analyte present in the initial sample. After the test is completed, the test strip can be discarded.

It should be emphasized that frequent measurements of blood glucose levels may be critical to the long-term health of many users. As a result, there is a need for blood glucose measuring systems that are reliable and easy to use.

Most analyte meters designed for home use are powered by batteries. There are occasions in which the batteries become depleted. In situations in which replacement batteries are not available, a user would not typically be able to conduct a test either as part of their typical regimen or instances (e.g., a heavy meal) in which a measurement should be taken.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2A illustrates an exploded view of an exemplary test strip;

FIG. 2B illustrates a top view of the exemplary test strip of FIG. 2A as assembled;

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Throughout the course of discussion and in order to provide a suitable frame of reference with regard to the accompanying drawings, certain terms are often used such as "upper", "lower", "proximal", "distal", "top", "bottom" and the like. These terms are not intended, unless specifically indicated, to affect the overall scope of the present invention.

As used herein, the terms "patient" or "user" refer to any human or animal subject and are not intended to limit the systems or methods to human use, although use of the subject invention in a human patient represents a preferred embodiment.

The term "sample" means a volume of a liquid, solution or suspension, intended to be subjected to qualitative or quantitative determination of any of its properties, such as the presence or absence of a component, the concentration of a component, e.g., an analyte, etc. The embodiments of the present invention are applicable to human and animal samples of whole blood. Typical samples in the context of the present invention as described herein include blood, plasma, red blood cells, serum and suspensions thereof.

The term "about" as used in connection with a numerical value throughout the description and claims denotes an interval of accuracy, familiar and acceptable to a person skilled in the art. The interval governing this term is preferably ±10%.

Unless specified, the terms described above are not intended to narrow the scope of the invention as described herein and according to the claims.

Figure 1A:
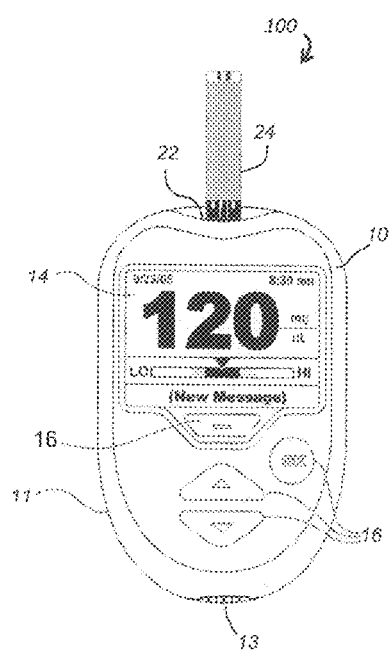
FIG. 1A illustrates a diagram of an exemplary test strip based analyte measurement system.

FIG. 1A illustrates an analyte measurement system 100 that includes an analyte or test meter 10. The analyte meter 10 is defined by a housing 11 that retains a data management unit ("DMU") 140 and further includes a port 22 sized for receiving a biosensor. According to one embodiment, the analyte meter 10 may be a hand held blood glucose meter and the biosensor is provided in the form of a test strip 24 insertable into the test strip port 22 for performing blood glucose measurements. The analyte meter 10 further includes a plurality of user interface buttons 16, and a display 14, such as an LCD display, as illustrated in FIG. 1A. A predetermined number of glucose test strips 24 may be stored in the housing 11 and made accessible for use in blood glucose testing. The plurality of user interface buttons 16 are associated with the DMU 140 and can be configured to allow the entry of data, to prompt an output of data, to navigate menus presented on the display 14, and to initiate execution of commands. Output data can include numerical values representative of analyte concentration presented on the display 14. Input information may include time and date information, information related to the everyday lifestyle of an individual, such as food intake, medication use, occurrence of health check-ups, and general health condition and exercise levels of an individual. These inputs can be requested via prompts presented on the display 14 and may be stored in a memory module of the analyte meter 10. Specifically and according to this exemplary embodiment, the user interface buttons 16 include markings, e.g., up-down arrows, text characters "OK", etc, which allow a user to navigate through the user interface presented on the display 14. Although the buttons 16 are shown herein as separate switches, a touch screen interface on display 14 with virtual buttons may also be utilized.

Figure 1B:
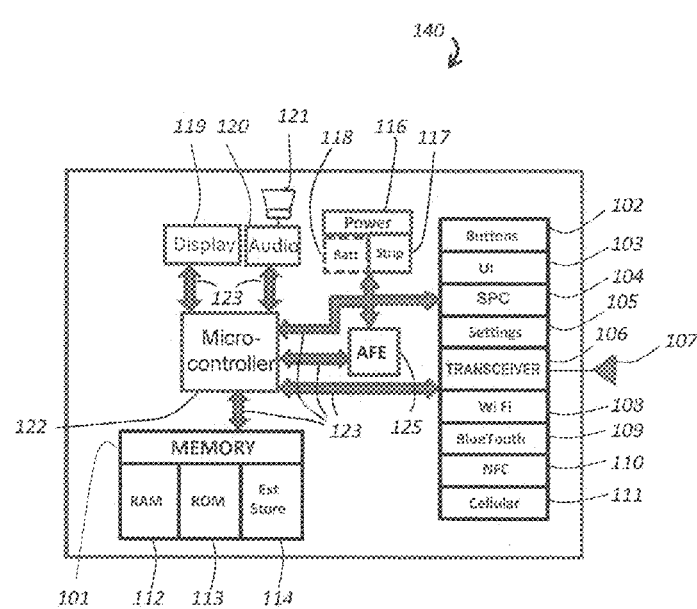
FIG. 1B illustrates a diagram of an exemplary processing system of the test strip based analyte measurement system of FIG. 1A.

The electronic components of the analyte measurement system 100 can be disposed on, for example, a printed circuit board situated within the housing 11 and forming the DMU 140 of the system described herein. FIG. 1B illustrates, in simplified schematic form, several of the electronic subsystems disposed within the housing 11 for purposes of this exemplary embodiment. The DMU 140 includes a processing unit 122 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below. The processing unit 122 is electrically connected to, for example, a test strip port connector 104 ("SPC") via an analog front end (AFE) subsystem 125. The AFE 125 is electrically connected to the strip port connector 104 during blood glucose testing. To measure a selected analyte concentration, the AFE 125 detects a resistance magnitude change across electrodes of the analyte test strip 24 which indicates that a sample, or control solution, has been applied thereto, using a potentiostat. At a predetermined time after the sample has been applied to the test strip 24 and has reacted with reagents therein, a preset voltage waveform is applied across the reacted sample via the electrodes which generates an electric current therethrough. The AFE 125 converts the electric current measurement into digital form for presentation on the display 14. The processing unit 122 can be configured to receive input from the strip port connector 104, analog front end subsystem 125, and may also perform a portion of the potentiostat function and the current measurement function.

The analyte test strip 24 can be in the form of an electrochemical glucose test strip, of which various embodiments are described below. The test strip 24 is defined by a nonporous substrate that can include one or more working electrodes. Test strip 24 can also include a plurality of electrical contact pads, where each electrode can be in electrical communication with at least one electrical contact pad. Strip port connector 104 can be configured to electrically engage the electrical contact pads, using its own electrical contacts in the form of prongs, and form electrical communication with the electrodes. The test strip 24 can include a reagent that is disposed on one or more interior surfaces of a sample receiving chamber or on electrodes within the sample receiving chamber of the test strip 24, such as a working electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose, or other analyte, in the applied fluid sample into an enzymatic by-product and in the process generate an amount of reduced mediator (e.g., ferrocyanide) that is proportional to the glucose concentration of the sample. The working electrode can then be used to apply a preset signal in the form of a voltage waveform to the sample and to measure a concentration of the reduced mediator in the form of an electric current. In turn, microcontroller 122 can convert the current magnitude into a glucose concentration in numerical units of milligrams/deciliter (mg/dL), for example, to be presented on the display 14. An exemplary analyte meter performing such current measurements is described in U.S. Patent Application Publication No. US 2009/0301899 A1 entitled "System and Method for Measuring an Analyte in a Sample", which is incorporated by reference herein as if fully set forth in this application.

A display module 119, which may include a display processor and display buffer, is electrically connected to the processing unit 122 over the electrical interface 123 for receiving and displaying output data such as alphanumeric text and graphical data, and for displaying user interface input options under control of processing unit 122. The structure of the user interface, such as menu options, is stored in user interface module 103 and is accessible by processing unit 122 for presenting menu options to a user of the blood glucose measurement system 100. An audio module 120 includes a speaker 121 for outputting audio data received or stored by the DMU 140. Audio outputs can include, for example, notifications, reminders, and alarms, or may include audio data to be replayed in conjunction with display data presented on the display 14. Such stored audio data can be accessed by processing unit 122 and executed as playback data at programmed times. A volume of the audio output is controlled by the processing unit 122, and the volume setting can be stored in settings module 105, as determined by the processor or as adjusted by the user. User input module 102 receives inputs via user interface buttons 16 which are processed and transmitted to the processing unit 122 over the electrical interface 123. The processing unit 122 may have electrical access to a digital time-of-day clock connected to the printed circuit board for recording time stamps corresponding to analyte measurements such as blood glucose measurements, which may include dates and times that can then be accessed, uploaded, or displayed at a later time, as necessary. Visual outputs on the display 14 can include, for example, notifications, reminders, and alarms, or may include visual outputs in conjunction with audio data played over the speaker 121.

A memory module 101, that includes but is not limited to volatile and non-volatile random access memory ("RAM") 112, a non-volatile memory 113, which may comprise read only memory ("ROM") or flash memory, and a circuit 114 for connecting to an external portable memory device, for example, via a data port 13, which may be a USB port, is electrically connected to the processing unit 122 over an electrical interface 123. External memory devices may include flash memory devices housed in thumb drives, portable hard disk drives, data cards, or any other form of electronic storage devices. The on-board memory can include various embedded applications and stored algorithms in the form of programs executed by the processing unit 122 for operation of the analyte meter 10. In particular, inputs to the processing unit 122 from the various modules described herein may be used to trigger reminders for the user to perform a blood glucose test, for example. On board memory can also be used to store a history of a user's blood glucose measurements including dates and times associated therewith. Using the wireless transmission capability of the analyte meter 10 or wired transmission via the data port 13, such measurement data can be transferred to connected computers or other processing devices.

A wireless module 106 may include transceiver circuits for wireless digital data transmission and reception via one or more internal antennas 107, and is electrically connected to the processing unit 122 over electrical interface 123. The wireless transceiver circuits may be in the form of integrated circuit chips, chipsets, programmable functions operable via processing unit 122, or a combination thereof. Each of the wireless transceiver circuits is compatible with a different wireless transmission standard. For example, a wireless transceiver circuit 108 may be compatible with the Wireless Local Area Network IEEE 802.11 standard known as WiFi. Transceiver circuit 108 may be configured to detect a WiFi access point in proximity to the analyte meter 10 and to transmit and receive data from such a detected WiFi access point. A wireless transceiver circuit 109 may be compatible with the Bluetooth protocol and is configured to detect and process data transmitted from a Bluetooth beacon in proximity to the analyte meter 10. A wireless transceiver circuit 110 may be compatible with the near field communication ("NFC") standard and is configured to establish radio communication with, for example, another NFC compliant device in proximity to the analyte meter 10. A wireless transceiver circuit 111 may comprise a circuit for cellular communication with cellular networks and is configured to detect and link to available cellular communication towers.

A power supply module 116 may be electrically connected to all modules in the housing 11 and to the processing unit 122 to supply electric power thereto. The power supply module 116 may comprise standard or rechargeable batteries 118. The power supply module 116 is also electrically connected to the processing unit 122 over the electrical interface 123 so that the processing unit 122 can monitor a power level remaining in a battery power mode of the power supply module 116. The processing unit 122 may be used to detect and output a battery level indication on the display 14 of the analyte meter 100 to indicate a current power level of the battery 118. The power level may be detected and output in digital form on the display 14 such as by illuminating corresponding indicator bars and, if the battery power is sufficiently depleted, the display and audio alarm output functions may be activated for indicating a low power condition.

In one embodiment, the battery 118 of the power supply 116 may be installed for limited use. As described below, a power source provided on the test strip 24 may be used to provide all the power necessary for performing an assay on a sample provided in the test strip 24. Hence, the analyte measurement system 100 may depend on a battery 118 of the power supply 116 to power various components, such as audio, transceiver, menu options, etc., while the test strip 24 supplies sufficient power to the meter for performing a sample assay. Another scenario in which embodiments disclosed herein may find use is when an analyte meter has unexpectedly depleted its battery power, or other power supply, such that it cannot supply sufficient power to complete a sample assay. The test strip embodiments disclosed herein may enable reliable operation of the analyte meter by supplying power for completion of the assay.

In another embodiment, a simplified measurement system 100 may be provided in which the analyte meter does not include a resident power source and is configured to receive sufficient power from a power source residing on the test strip 24 to perform a sample assay and display results for a finite time on the display 14 of the analyte measurement system 100. Such a simplified design for the measurement system 100 may further eliminate a typical detection circuit that, for example, senses the insertion of a passive test strip into the test strip port 22. A person of ordinary skill in the art will understand that various combinations of functions may be provided by the meter under its own battery power and that various functions may be powered by the test strip supplied power source. It is contemplated that a simplified analyte meter 10 may also be manufactured which requires no internal power source and is dependent on a test strip power source to supply power to the analyte meter.

In general, with reference to FIGS. 2A-2B, the test strip 24 comprises an inlet 227 for receiving a sample at a distal end 213 of the test strip 24. The inlet 227 leads to a sample chamber 226 in direct communication with electrodes 220-222. The sample chamber 226 includes an exposed reagent layer 228 that reacts with a sample applied therein. The microcontroller 122 of the analyte meter 10 programmably generates electrical signals for performing an assay on the reacted sample via electrical communication with electrodes 220-222. A voltage signal is transmitted through the sample via a first working electrode, for example, and a sample response signal is measured thereby, such as at the second working electrode, to determine an analyte concentration of the sample. The battery 203 that is assembled within the test strip 24 supplies power to the analyte meter 10 for performing the sample assay. The test strip 24 can have various configurations, but is typically in the form of one or more rigid or semi-rigid layers having sufficient structural integrity to allow handling and connection to an analyte measurement system, as will be discussed in further detail below. The test strip 24 may be formed from various materials, including plastic and other insulating materials, and may be assembled using adhesive coatings on the various layers. The material of the various layers, other than the reagent layer 228, typically is one that is insulating (non-conductive) and may be inert and/or electrochemically non-functional, wherein they do not readily corrode over time nor chemically react with a sample applied in the sample chamber 226.

With reference to FIGS. 2A-2B in more detail, test strip 24 includes a plurality of layers generally defined by a planar construction. A bottom layer 229 is made from an insulating substrate 230. The distal end 213 of the substrate 230 further includes an insulator layer 225 and a reagent layer 228 deposited thereon. The reagent layer 228 can be formed from various materials, including various mediators and/or enzymes. Suitable mediators include, by way of non-limiting example, ferricyanide, ferrocene, ferrocene derivatives, osmium bipyridyl complexes, and quinone derivatives. Suitable enzymes include, by way of non-limiting example, glucose oxidase, glucose dehydrogenase (GDH) based on pyrroloquinoline quinone (PQQ) co-factor, GDH based on nicotinamide adenine dinucleotide co-factor, and FAD-based GDH. One exemplary reagent formulation, which would be suitable for making the reagent layer 228, is described in U.S. Pat. No. 7,291,256, entitled "Method of Manufacturing a Sterilized and Calibrated Biosensor-Based Medical Device," the entirety of which is hereby incorporated as if fully set forth herein by reference. The reagent layer 228 can be formed using various processes, such as slot coating, dispensing from the end of a tube, ink jetting, and screen printing. While not discussed in detail, a person skilled in the art will also appreciate that the reagent disclosed herein can also contain a buffer, a wetting agent, and/or a stabilizer.

A plurality of contact pads 215-219 are disposed at a proximal end 231 of the substrate 230, which is at the end of the test strip 24 that is inserted into the test strip port 22 of the analyte meter 10. A plurality of electrodes extending from the contact pads at the proximal end 231 of the substrate 230 to the distal end 213 of the substrate 230 include a counter electrode 220 electrically connected to the counter electrode contact pad 216; a first working electrode 221 electrically connected to first working electrode contact pad 217; and a second working electrode 222 electrically connected to second working electrode contact pad 218. The electrodes 220-222 are exposed to the sample chamber 226 for making direct electrical contact with a reacted sample after the sample is applied in the sample chamber 226. The electrically conductive pattern forming the electrical contact pads 215-219 and electrodes 220-222 can be formed from any conductive material, including inexpensive materials, such as aluminum, carbon, graphene, graphite, silver ink, tin oxide, indium oxide, copper, nickel, chromium and alloys thereof. However, precious metals that are conductive, such as palladium, platinum, indium tin oxide or gold, can optionally be used. The conductive layer may be deposited onto the substrate layer 230 by various processes, such as sputtering, electroless plating, thermal evaporation and screen printing.

An insulating material layer 205 is adhered to the bottom layer 229, at the distal end 213 thereof, over at least a portion of the insulating layer 225, reagent layer 228, and over a portion of the electrodes 220-222. The insulating layer 205 has an opening formed therein positioned above the reagent layer 228, which defines interior walls of a sample chamber 226 that is in communication with the reagent layer 228 and the electrodes 220-222. A top protective layer 201 and the insulating layer 225 form top and bottom surfaces of the sample chamber 226, respectively. The sample chamber 226, reagent layer 228 and electrodes 220-222 thus form an electrochemical cell, when a fluid sample is provided in the chamber 226, and is electrically coupled to an analyte measurement system or device. A person skilled in the art will appreciate that the electrical contact pads 215-219 and the electrodes 220-222 can have a variety of configurations other than those illustrated. The test strip 24 may include additional layers other than those illustrated herein.

In one exemplary embodiment, the volume of the sample chamber can range from about 0.1 microliters to about 5 microliters, preferably about 0.2 microliters to about 3 microliters, and more preferably about 0.2 microliters to about 0.4 microliter. To provide the small volume, the inlet 227 can have an area ranging from about 0.005 $cm^2$ to about 0.2 $cm^2$, preferably about 0.0075 $cm^2$ to about 0.15 $cm^2$, and more preferably about 0.01 $cm^2$ to about 0.08 $cm^2$, and the thickness of the insulating layer 205 can range from about 1 micron to 500 microns, and more preferably about 10 microns to 400 microns, and more preferably about 40 microns to 200 microns, and even more preferably about 50 microns to 150 microns. As will be appreciated by those skilled in the art, the volume of the sample chamber and the area of the inlet 227 can vary significantly.

For purposes of the exemplary embodiment, a thin profile battery 203 having voltage terminals 207 may be adhered to the bottom layer using conductive adhesive such that battery terminals 207 are each electrically connected to one of the contact pads 215, 219. The top non-conductive protective layer 201 covers the test strip 24 leaving exposed contact pads 215-219, as shown in the completed test strip assembly of FIG. 2B.

Figure 3:
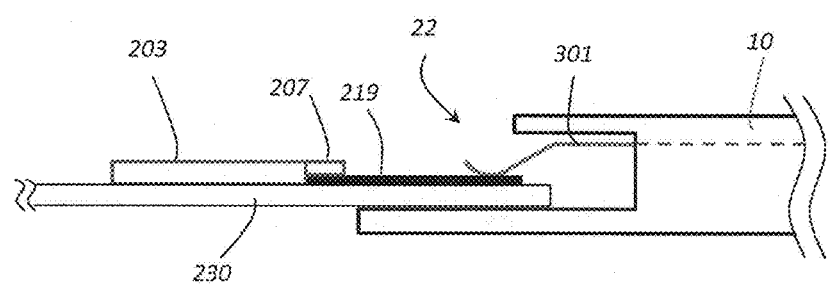
FIG. 3 illustrates a side view of the test strip of FIGS. 2A-2B inserted in a test strip port.

With reference to the figures now inclusive of FIG. 3, electrical contacts in the analyte meter 10 are formed as prongs 301 to electrically connect with the contact pads 215-219 of the test strip 24 when the proximal end 231 of the test strip 24 is inserted in the test strip port 22 of the analyte meter 10. As illustrated in FIG. 3, the analyte meter 10 that receives the test strip 24 in its test strip port 22 engages the electrical contact pads, e.g. contact pad 223 in FIG. 3, using metallic prongs 301 that engage corresponding contact pads 215-219 of the test strip 24. The prongs 301 comprise flexible spring arms which may be fabricated from a conductive metallic material which flex to allow insertion of the test strip 24 so that the contact pads 215-219 establish a sufficient ohmic contact with the exemplary prongs 301 of the analyte meter 10.

Although the side view of FIG. 3 visibly illustrates one contact pad 219 and one electrical prong 301, it will be understood that remaining contact pads 215-218 are disposed adjacent to the contact pad 219 (as illustrated in FIGS. 2A-2B) as well as additional prongs 301 being disposed in the analyte meter 10 for each of the contact pads 215-19. Thus, the analyte meter 10 is electrically connected to corresponding electrodes 220-222, which allows electrical communication between the microcontroller 122 and the test strip electrodes 220-222.

Two of the prongs 301 of the analyte meter 10 are connected internally to strip port power supply 117 of the analyte meter power supply module 116. These prongs 301 each engage one end of the power supply contact pads 215, 219 of the test strip 24 which deliver electrical power in the form of electrical voltage and current to the analyte meter 10 when the test strip 24 is inserted in test strip port 22. Another end of the power supply contact pads 215, 219, in turn, are each electrically connected to one of the battery terminals 207, when the test strip is assembled, and thereby supply the power in the form of the electrical voltage and current from the battery 203 to the analyte meter 10.

It has been demonstrated by electrical tests that a single sample assay performed by analyte meter 10, and an analyte concentration determined thereby to be presented on a display 14 of the analyte meter 10, may require a maximum of about five (5) minutes of meter run time at a maximum current of about 50 mA, thus requiring a battery 203 that is capable of storing about 4.2 mAh (milli-amp hours) of electrical charge (energy capacity). Thus, fabricating the test strip 24 using a thin profile battery having a sufficient energy capacity results in a test strip capable of delivering power to an analyte meter 10 such that the analyte meter 10 itself requires no other power source to complete a sample assay. Examples of commercially available batteries having sufficient energy capacity and a format compatible with assembly of test strip 24 include an ultra thin lithium manganese dioxide cell (Part No. CP452922) manufactured by GMB Co., Ltd., of China; and a zinc-manganese dioxide based alkaline paper battery made by Power Paper, Ltd., of Israel. These example thin profile batteries are manufactured on thin film substrates such as paper or polymer and have a thickness of less than about 0.5 mm, an energy density from about 2.5 mAh/cm$^2$ to about 5 mAh/cm$^2$, and supply voltages of about 1.5 V to about 4 V. Exemplary battery types include lithium polymer, lithium manganese dioxide, and lithium thionyl chloride. As shown in FIG. 2A, such a thin film battery 203 may have its terminals 207 each connected to one end of contact pads 215, 223 using, for example, a conductive adhesive.

Figure 4:
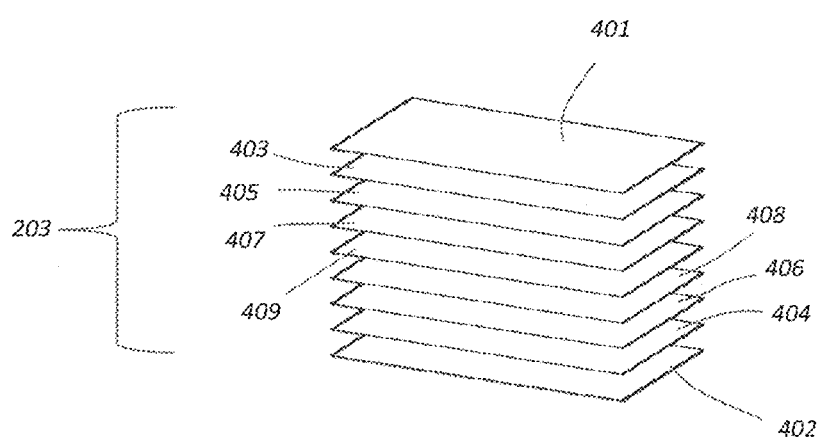
FIG. 4 illustrates an alternative method of fabricating an integrated battery within the test strip of FIGS. 2A-2B.

With reference to FIG. 4, there is illustrated an alternative method for fabricating an integrated battery 203 within the test strip 24. Although the integrated battery 203 has been described herein as being prefabricated using commercially available embodiments, an alkaline type battery 203 may be formed directly over the electrodes 215-219 on the bottom layer 229 of the test strip 24 as follows. An insulating layer 402 is first applied over the electrodes 215-219 on the substrate 230 followed by a metallic current collector layer 404, such as aluminum, over the insulating layer 402. This is followed by forming a zinc anode layer 406 over the current collector 404, and then an electrolyte layer 408 over the current collector 404. These steps complete the formation of the anode terminal. An insulating separator layer 409 is applied to the anode terminal thus formed. The cathode terminal is formed next as follows in a sequence that is symmetrical to the anode formation. A second electrolyte layer 407 is formed over the separator layer 409, followed by a manganese-dioxide cathode layer 405 over the electrolyte layer 407. Another metallic current collector layer 403, such as aluminum, is formed over the cathode layer 405. A top insulating layer 401 is formed over the current collector layer 403. The top protective layer 201 described above may be used as the insulating layer 401, or the top protective layer 201 may be used in addition to the top insulating layer 401.

The battery 203 may be fabricated, using the steps as described above, before or after the insulating layer 205 is applied to the bottom layer 229 for forming the sample chamber 226. The battery layers 401-409 may be formed using various processes, such as sputtering, electroless plating, thermal evaporation and screen printing.

Figure 5:
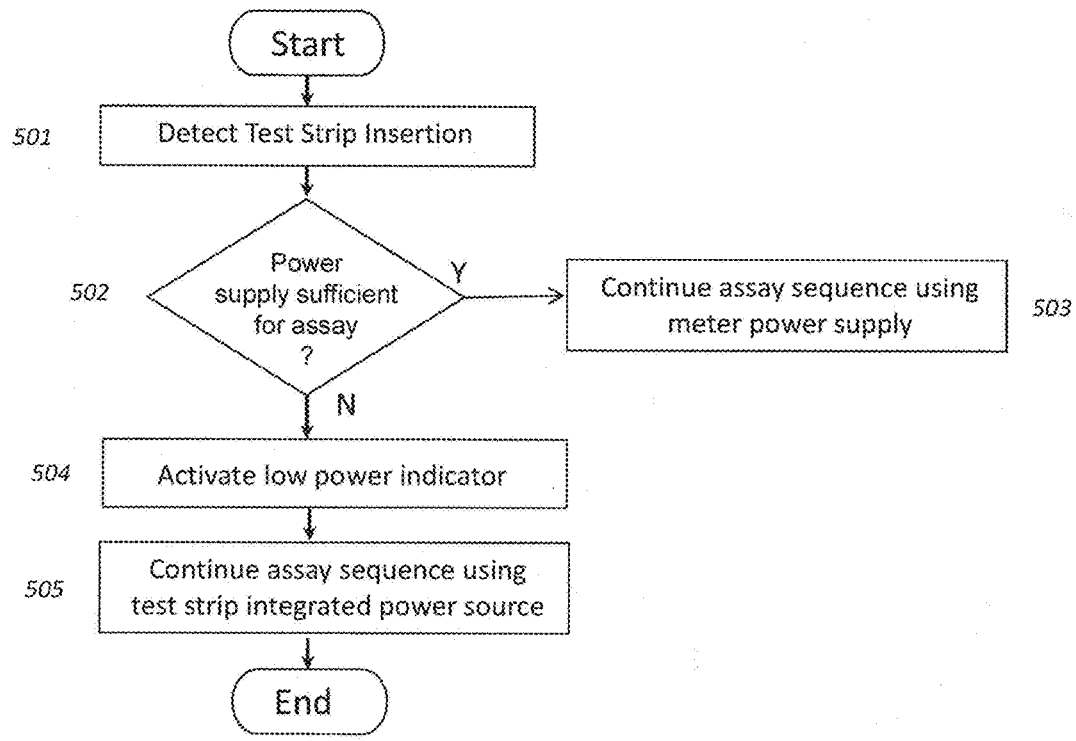
FIG. 5 illustrates a flowchart depicting a method of operating an analyte measurement system.

With reference to FIG. 5, a flowchart is illustrated that demonstrates a method performed by the analyte measurement system 100 which is triggered at step 501 when a test strip 24 is inserted in test strip port 22. Because the power supply contact pads 215, 219 are connected to the integrated power source 203 of the test strip, a voltage signal is received at the analyte meter SPC 105 when its contacts 301 engage the power supply contact pads 215, 219. This voltage signal is detected at the SPC 104 and the microcontroller 122 determines that the test strip 24 has been inserted. At step 502 the microcontroller 122 determines whether the battery power supply 118 is at a high enough level to deliver sufficient power for completing an assay on a sample provided by a user in the inserted test strip 24. The power supply level required to perform an assay on the sample may be determined beforehand and stored in on board memory 101 which the microcontroller 122 accesses to make the determination. If the microcontroller 122 determines that the power level is sufficient at step 502, then the analyte measurement system 100 continues its usual sequence of performing an assay using the internal battery power supply 118 at step 503.

If the microcontroller 122 determines that the magnitude of the power level is insufficient to perform an assay at step 502, then the analyte measurement system 100 displays a low power (low voltage) indication on display 14 at step 504, which may include a visual indication combined with an audible notification using speaker 121. In response to the low voltage determination, the integrated power source 203 provided by the test strip 24 is capable of enabling the analyte measurement system 100 to perform the assay using only the power supplied by the integrated power source 203. At step 505, the analyte measurement system 100 continues its usual sequence of performing an assay using power provided by the integrated power source 203 in the test strip 24 via engagement with the power supply contact pads 215, 219.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," 'subsystem" and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Furthermore, the various methods described herein can be used to generate software codes using off-the-shelf software development tools. The methods, however, may be transformed into other software languages depending on the requirements and the availability of new software languages for coding the methods.

PARTS LIST FOR FIGS. 1A-5

10 analyte meter
11 housing, meter
13 data port
14 display
16 user interface buttons
22 test strip port
24 test strip
100 analyte measurement system
101 memory module
102 buttons module
103 user interface module
104 strip port connector
105 microcontroller settings module
106 transceiver module
107 antenna
108 WiFi module
109 Bluetooth module
110 NFC module
111 Cellular Module
112 RAM module
113 ROM module
114 external storage
116 power supply module
117 test strip power supply
118 battery power supply
119 display module
120 audio module
121 speaker
122 microcontroller (processing unit)
123 communication interface
125 analog front end subsystem
140 data management unit
201 top protective layer (tape)
203 test strip battery
205 insulating material layer
207 test strip battery terminals
213 test strip distal end
215 electrical contact pad—power supply terminal
216 electrical contact pad—counter electrode
217 electrical contact pad—first working electrode
218 electrical contact pad—second working electrode
219 electrical contact pad—power supply terminal
220 counter electrode
221 first working electrode
222 second working electrode
225 insulating layer
226 sample chamber
227 sample chamber inlet
228 reagent layer
229 bottom layer (substrate)
230 bottom layer substrate
231 test strip proximal end
301 electrical contact—analyte meter
401 top insulating layer—battery
402 bottom insulating layer—battery
403 current collector layer—cathode
404 current collector layer—anode
405 manganese-dioxide cathode layer
406 zinc anode layer
407 electrolyte layer—cathode
408 electrolyte layer—anode
409 separator layer
501 step—detect strip insertion
502 step—is power supply sufficient for assay?
503 step—continue assay sequence using meter power supply
504 step—activate low power indicator
505 step—continue assay sequence using test strip integrated power source While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A test strip for use with an analyte meter, the test strip comprising:
   a substantially planar substrate;
   a sample chamber formed in the substrate and configured for receiving a sample from a user; and
   an integrated power source configured for providing electrical power to the analyte meter upon insertion of the test strip therein, thereby enabling the meter to be sufficiently powered to perform an assay on the sample using only the electrical power provided by the test strip.

2. The test strip of claim 1, wherein the integrated power source comprises at least one battery.

3. The test strip of claim 2, wherein the at least one battery is at least one of the group comprising a lithium ion battery, lithium polymer battery, lithium manganese dioxide battery, lithium thionyl chloride battery, and a paper battery.

4. The test strip of claim 1, wherein said substrate comprises a plurality of elongated planar layers, and wherein the integrated power source comprises at least a portion of at least one of the planar layers.

5. The test strip of claim 4, further comprising electrical contact pads connected to the integrated power source, the contact pads being configured to engage electrical contacts of the analyte meter upon insertion therein.

6. The test strip of claim 5, wherein the electrical contact pads are at least a portion of one of the planar layers.

7. The test strip of claim 2, wherein the test strip further comprises an electrode for applying a first electric signal to the sample, the first electric signal generated by the analyte meter using the power provided by the at least one battery.

8. The test strip of claim 7, wherein the test strip further comprises an electrical contact pad connected to the analyte meter for receiving the first electric signal from the analyte meter.

9. The test strip of claim 8, wherein the test strip further comprises a second electrical contact pad connected to the analyte meter for transmitting a second electric signal to the analyte meter, the second electric signal generated by the sample in response to the first electric signal.

10. The test strip of claim 9, wherein the at least one battery comprises sufficient energy capacity to energize a display of the analyte meter to present thereon an analyte concentration value corresponding to the second electric signal.

11. An analyte measurement system comprising:
a test strip comprising a sample chamber for receiving a sample from a user, an integrated power source, and contact pads electrically connected to the integrated power source; and
an analyte meter comprising electrical contacts that engage the contact pads of the test strip upon insertion of the test strip in the analyte meter so that the analyte meter receives power from the power source to perform an assay upon the sample from the user.

12. The analyte measurement system of claim 11, wherein the electrical contacts provide a detectable electric signal to the analyte meter indicating the insertion of the test strip in the analyte meter.

13. The analyte measurement system of claim 12, wherein the detectable electric signal is a voltage level of the power from the power source.

14. The analyte measurement system of claim 11, wherein the power source comprises at least one battery.

15. A method for enabling an analyte measurement system, said method comprising:
inserting a test strip into an analyte meter, the test strip comprising an integrated power source capable of enabling the analyte meter to perform an assay; and
the analyte meter engaging power supply contacts of the test strip, the power supply contacts electrically connected to the integrated power source.

16. The method of claim 15, further comprising the analyte meter determining a power supply level of an internal power supply of the analyte meter.

17. The method of claim 16, further comprising the analyte meter using the internal power supply to perform the assay in response to determining that the internal power supply level is above a preselected magnitude.

18. The method of claim 15, further comprising the analyte meter detecting the insertion of the test strip in response to a detected voltage level of the power supply contacts of the test strip.

19. The method of claim 16, further comprising displaying a low voltage indication on a display of the analyte meter in response to determining that the internal power supply level is insufficient to perform the assay.

20. The method of claim 19, further comprising using power provided by the integrated power source via the power supply contacts of the test strip to perform the assay in response to said determining that the internal power supply level is insufficient to perform the analyte measurement.

* * * * *